United States Patent
Swoyer et al.

(10) Patent No.: US 7,238,182 B2
(45) Date of Patent: Jul. 3, 2007

(54) DEVICE AND METHOD FOR TRANSURETHRAL PROSTATE TREATMENT

(75) Inventors: John M. Swoyer, Andover, MN (US); Thomas R. Skwarek, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 382 days.

(21) Appl. No.: 10/423,393

(22) Filed: Apr. 25, 2003

(65) Prior Publication Data

US 2004/0215179 A1   Oct. 28, 2004

(51) Int. Cl.
*A61B 18/18* (2006.01)

(52) U.S. Cl. .................. 606/41; 607/101; 128/898

(58) Field of Classification Search ............ 606/27–52; 607/96, 98–101, 102; 128/898; 600/135, 600/564–565, 570–571
See application file for complete search history.

(56) References Cited

U.S. PATENT DOCUMENTS

| | | | | |
|---|---|---|---|---|
| 4,685,458 A * | 8/1987 | Leckrone | ................ | 606/7 |
| 5,370,675 A * | 12/1994 | Edwards et al. | ............ | 607/101 |
| 6,214,024 B1 * | 4/2001 | Houser | ................ | 606/170 |
| 6,241,702 B1 | 6/2001 | Lundquist | | |
| 6,325,798 B1 * | 12/2001 | Edwards et al. | ............ | 606/41 |
| 6,514,247 B1 | 2/2003 | McGaffigan | | |
| 6,558,382 B2 * | 5/2003 | Jahns et al. | ................ | 606/41 |
| 6,652,518 B2 * | 11/2003 | Wellman et al. | ............ | 606/41 |
| 6,692,490 B1 * | 2/2004 | Edwards | ................ | 606/41 |
| 2002/0177847 A1 | 11/2002 | Long | | |
| 2002/0193705 A1 * | 12/2002 | Burbank et al. | ............ | 600/562 |
| 2002/0193781 A1 * | 12/2002 | Loeb | ................ | 606/15 |
| 2003/0181904 A1 * | 9/2003 | Levine et al. | ............ | 606/45 |
| 2004/0162572 A1 * | 8/2004 | Sauer | ................ | 606/170 |

* cited by examiner

*Primary Examiner*—Michael Peffley
(74) *Attorney, Agent, or Firm*—Scott A. Marks; Mary P. Bauman

(57) ABSTRACT

The invention provides a transurethral ablation device comprising a catheter sized for insertion into a urethra of a male patient. A distal end of the catheter defines a lateral cavity. A vacuum line applies vacuum pressure to the cavity to capture a portion of the urethra and a portion of the prostate into the cavity. An ablation probe has a distal tip mounted within the catheter adjacent the cavity, and is movable for insertion into the captured portion of the prostate. The ablation probe can be inserted with an orientation substantially parallel to the urethral wall. Alternatively, multiple ablation probes can be provided for simultaneous use in ablating tissue with a target site in the prostate. A suction cannula may be used to remove ablated tissue from the target site.

40 Claims, 10 Drawing Sheets

DEVICE AND METHOD FOR TRANSURETHRAL PROSTATE TREATMENT

FIELD OF THE INVENTION

The invention relates generally to prostate treatment and, more particularly, to techniques for transurethral treatment of benign prostatic hypertrophy (BPH).

BACKGROUND

Benign prostatic hypertrophy or hyperplasia (BPH) is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling.

One surgical procedure for treating BPH is transurethral needle ablation (TUNA). The TUNA technique involves transurethral delivery of an electrically conductive needle to the prostate site. The needle penetrates the prostate in a direction generally perpendicular to the urethral wall, and delivers electrical current to ablate prostate tissue. The electrical current heats tissue surrounding the needle tip to destroy prostate cells, and thereby create a lesion within the prostate gland. The destroyed cells may be absorbed by the body, infiltrated with scar tissue or become non-functional.

Other transurethral ablation procedures involve delivery of microwave, radio frequency, acoustic, and light energy to the prostate gland. In addition, some procedures involve delivery of localized chemotherapy, drug infusions, collagen injections, or injections of agents which are then activated by light, heat or chemicals to destroy prostate tissue. These procedures, as well as the TUNA procedure, pose the risk of trauma to the urethral wall. In addition, the precision and uniformity of the procedures in terms of the ability to target specific prostate tissue raises challenges. In addition, ablation of specific shapes and volumes of prostate tissue continues to be difficult.

U.S. Published Patent Application No. 2002/0177847, to Long, describes an endoscopic ablation system with a side opening that pulls esophageal tissue into contact with ablation electrodes using vacuum pressure. U.S. Pat. No. 6,514,247 to McGaffigan et al. discloses a transurethral needle ablation device. U.S. Pat. No. 6,241,702 to Lundquist et al. describes another transurethral ablation needle device. Table 1 below lists documents that disclose devices for transurethral ablation of prostate tissue.

TABLE 1

| Pat. No. | Inventors | Title |
| --- | --- | --- |
| 2002/0177847 | Long | Endoscopic ablation system with flexible coupling |
| 6,514,247 | McGaffigan et al. | Transurethral needle ablation device with aligned handle |
| 6,241,702 | Lundquist et al. | Radio frequency ablation device for treatment of the prostate |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY

The present invention is directed to a device and method for transurethral ablation of prostate tissue, e.g., to alleviate BPH. The invention has certain objects. That is, various embodiments of the present invention provide solutions to one or more problems existing in the prior art with respect to the ablation of prostate tissue.

The problems include, for example, undesirable labor, time, and lack of precision associated with some existing transurethral ablation techniques. In existing techniques, such as the TUNA procedure, electrode needles are deployed perpendicular to the urethral wall to penetrate prostate tissue to be ablated. The needles generally form lesions with an elongated oval shape that extends perpendicular to the urethra wall. As a result, multiple lesion planes are often required for complete treatment along the length of the BPH tissue, requiring additional steps and time to perform the procedure. In addition, the perpendicular lesions tend to ablate not only BPH tissue but also healthy prostatic tissue as well, presenting imprecision. Another problem with perpendicular ablation is the extended period of time often required for the ablated tissue to be reabsorbed by the body.

Various embodiments of the present invention have the object of solving at least one of the foregoing problems. For example, it is an object of the present invention to overcome at least some of the disadvantages of the foregoing procedures by providing a transurethral ablation procedure capable of forming lesions substantially parallel to the urethral wall. It is a further object of the invention to provide transurethral ablation procedure that permits removal of ablated tissue. As another object, the invention provides a transurethral ablation procedure that makes use of multiple ablation probes.

Various embodiments of the invention may possess one or more features capable of fulfilling the above objects. In general, the invention provides a transurethral ablation device comprising a catheter sized for insertion into a urethra of a male patient. A distal end of the catheter defines a lateral cavity. A vacuum line applies vacuum pressure to the cavity to capture a portion of the urethra and a portion of the prostate into the cavity. An ablation probe has a distal tip mounted within the catheter adjacent the cavity, and is movable for insertion into the captured portion of the prostate. In some embodiments, the ablation probe is inserted with an orientation substantially parallel to the urethral wall. In other embodiments, multiple ablation probes can be provided for simultaneous use in ablating tissue with a target site in the prostate. According to further embodiments, a suction cannula removes ablated tissue from the target site.

The invention also provides transurethral ablation procedure embodied by a method for use of the ablation device described above. The method involves, for example, inserting a distal end of a catheter into a urethra of a male patient, wherein the distal end of the catheter defines a lateral cavity. The distal end of the catheter is moved to a position within the urethra proximate to the prostate, vacuum pressure is applied to the cavity to capture a portion of the urethra and a portion of the prostate into the cavity. An ablation probe is inserted into the captured portion of the prostate via the catheter, tissue within the prostate is ablated via the ablation probe. In addition, the ablated tissue may be removed from the prostate via a suction cannula.

In comparison to known implementations of transurethral prostate ablation, various embodiments of the present invention may provide one or more advantages. For example, the invention may reduce the number of steps involved in the procedure. In particular, the formation of lesions with an orientation substantially parallel to the urethral wall permits a greater extent of the prostate to be treated in a single step and in a reduced amount of time. In addition, the parallel orientation of the ablation probe can provide improved precision and avoid significant ablation of the urethral wall. As a further advantage, ablated tissue can be removed from the prostate via a suction cannula, rather than left for reabsorption by the body, thereby accelerating the effects of the ablation procedure in treating BPH. For example, active withdrawal of ablated tissue can provide an immediate reduction in the mass, and possibly volume, of the prostate.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
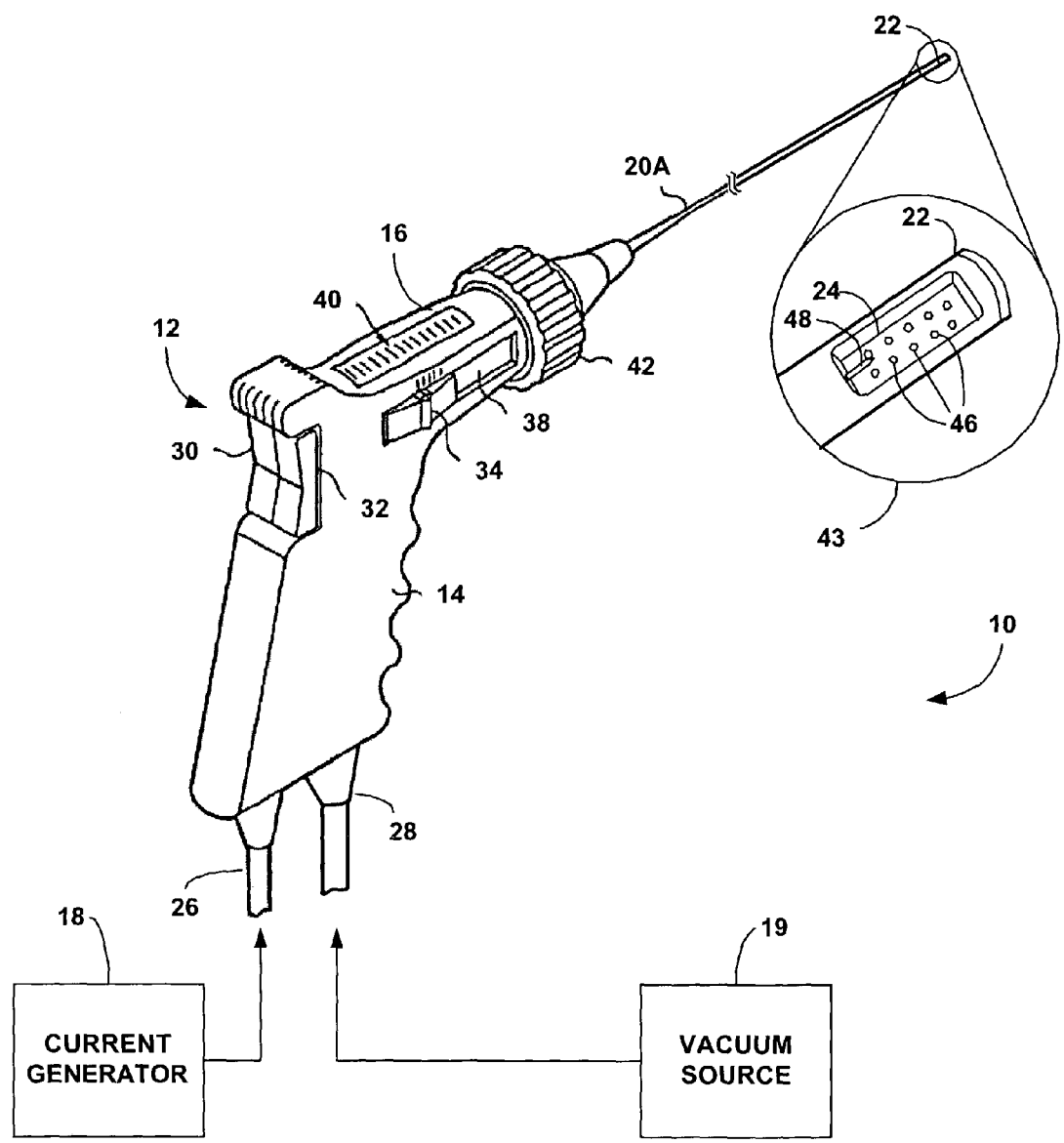
FIG. 1 is a schematic diagram illustrating a device for transurethral ablation of prostate tissue in accordance with the invention.

FIG. 1 is a schematic diagram illustrating a device 10 for transurethral ablation of prostate tissue in accordance with the invention. As shown in FIG. 1, device 10 includes a manipulator 12 having a handle 14, a barrel 16, a current generator 18, a vacuum source 19, and a transurethral ablation catheter 20A extending from the barrel. Catheter 20A is sized for insertion into a urethra of a male patient. As will be described, distal end 22 of catheter 20A defines a lateral cavity 24 to capture a portion of the urethral wall and prostate for the ablation procedure. Cavity 24 serves for positioning and fixation of tissue to be ablated.

Current generator 18 delivers electrical current to manipulator 12 via an electrical connector 26. Manipulator 12 includes internal electrical conductors to transmit the electrical current to catheter 20A. Similarly, catheter 20A includes one or more electrical conductors to transmit the electrical current to distal end 22 for use in generating ablation energy. Vacuum source 19 applies vacuum pressure via vacuum connector 28 of manipulator 12. Manipulator 12 and catheter 20A transmit the vacuum pressure to cavity 24 at distal end 22 to assist in tissue capture.

In the example of FIG. 1, manipulator 12 includes rocker switches 30, 32. Switch 30 permits a surgeon to control the application of electrical current supplied by current generator 18. Switch 32 permits the surgeon to control the application of vacuum pressure to cavity 24. Alternatively, current generator 18, vacuum pressure, or both may be activated using a conventional foot switch. A slider bar 34, disposed in channel 38, permits the surgeon to move an ablation probe longitudinally within catheter 20A. An indicator 40 tracks the movement of the ablation probe for overhead visibility by the surgeon. Wheel 42 permits rotation of catheter 20A, e.g., to place cavity 24 at desired radial positions within the urethra.

As shown in the enlarged view 43 of distal end 22, cavity 24 defines a substantially rectangular orifice or cavity with a major axis extending longitudinally relative to catheter 20A. However, other shapes for cavity 24 are possible. In general, cavity 24 is sized and shaped to permit capture of a substantial amount of urethral and prostate tissue for ablation. Cavity 24 includes a plurality of vacuum ports 46 coupled to vacuum source 19. In addition, an ablation probe 48 extends into cavity 24.

Upon deployment of distal end 22 of catheter 20A to a position within the urethra proximate to the prostate, and rotation of the catheter to a desired radial position, vacuum source 19 applies vacuum pressure to vacuum ports 46 to draw the urethral and prostate tissue into cavity 24. As an example, vacuum source 19 may apply an overall negative pressure in the range of approximately 300 to 400 mm/Hg in order to capture the target tissue. Exemplary dimensions of the cavity 24, e.g., for an 18 French catheter, are approximately 4 to 6 mm deep, 4 to 6 mm in width and 20 to 35 mm in length. In some embodiments, a removable cover may be provided to cover the cavity 24 until the catheter reaches the prostate. The number and shape of vacuum ports 46, and the pressure applied by each vacuum port, may vary.

While vacuum source 19 maintains vacuum pressure, the surgeon extends ablation probe 48 into the captured tissue with an orientation substantially parallel to the urethral wall. Ablation probe 48 is delivered into prostatic tissue underneath or behind the prostatic urethra. Ablation probe 48 ablates the prostatic tissue beneath the prostatic urethra substantially parallel to the urethra and proximal to the prostatic urethra. Following ablation a suction cannule may be introduced to remove the ablated tissue, and thereby accelerate the therapeutic effects of the transurethral ablation procedure. As an alternative to suction via a suction cannula, ablated tissue may be removed using an auger-like mechanical device.

In the example of FIG. 1, ablation probe 48 is an ablation needle that carries electrical current delivered by current generator 18. Alternatively, as will be described, ablation probe 48 may deliver microwave energy, laser energy, or chemical agents to ablate tissue. In general, the electrical current may be selected to provide pulsed or sinusoidal waveforms, cutting waves, or blended waveforms. In addition, the electrical current may include ablation current followed by current sufficient to cauterize blood vessels. The electrical current may be accompanied by delivery of electrolytes to yield desired conduction characteristics, as well as pain relief substances such as Lidocaine to reduce pain experienced by the patient during the course of the procedure.

The electrical current may be selected to produce power in the range of 5 to 15 watts, and can be applied for a duration of approximately 30 to 120 seconds. If electrocautery current is also provided, the power may be as high as 300 watts. Electrical current flows between ablation probe 48 and a reference electrode placed within or on the surface of the patient's body. Alternatively, ablation probe 48 may take the form of a bipolar probe that carries two or more electrodes, in which case the current flows between the electrodes.

The parallel orientation of ablation probe 48 serves to create a substantially parallel lesion within the prostate tissue, and can reduce undesirable ablation of urethral tissue, providing greater precision. In addition, the volume and shape of the lesion extends longitudinally within the prostate tissue, enabling ablation of a greater extent of prostate tissue in a single step. In particular, the longitudinally-oriented lesion can relieve more of the constriction created by BPH along the length of the urethra. In other words, the lesion reduces pressure along the length of the prostatic urethra and provides less flow resistance when passing urine. Device 10 enables the transurethral ablation procedure to be completed in a reduced number of steps In some embodiments, a suction cannula or auger-like device may be deployed to actively remove ablated tissue from the target site, accelerating the therapeutic effects of the ablation procedure.

Figure 2:
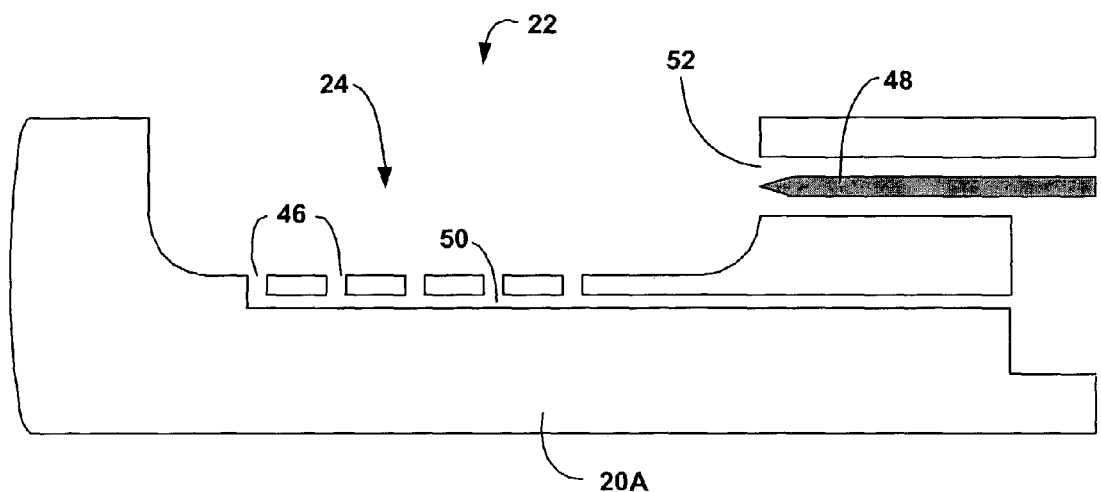
FIG. 2 is an enlarged side view of the distal end of the device of FIG. 1.
Figure 3:
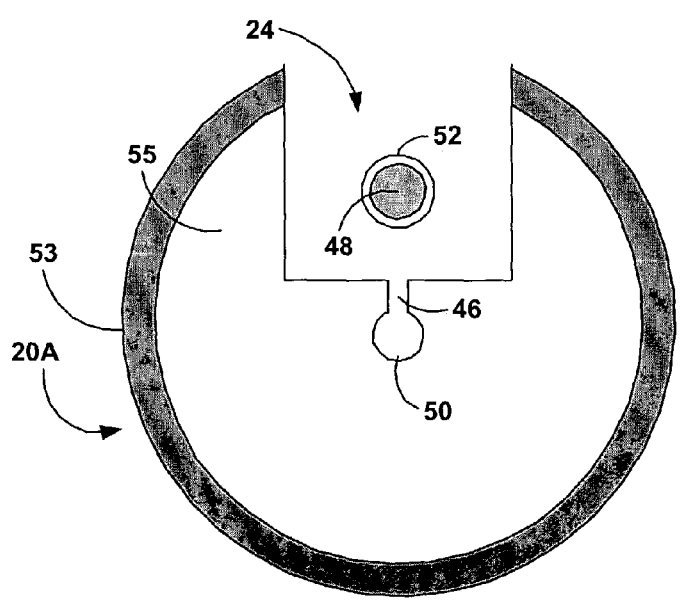
FIG. 3 is a cross-sectional view of the distal end of the device of FIG. 1.

FIG. 2 is an enlarged side view of distal end 22 of catheter 20A of device 10 of FIG. 1. FIG. 3 is a cross-sectional end view of distal end 22 of catheter 20A. As shown in FIGS. 2 and 3, catheter 20 defines cavity 24 and multiple vacuum ports 46. Vacuum ports 46 are coupled to a vacuum line 50. Vacuum line 50 extends along the length of catheter 20A for communication with vacuum source 19. An internal lumen 52 defines a channel for introduction of ablation probe 48 into cavity 24. Catheter 20A includes an outer catheter wall 53, which may be coated with a lubricious material, such as PTFE or silicone, to facilitate travel of the catheter within the urethra. An inner core 55 of catheter 20A may be molded to define various lumens, such as vacuum line 50 and introduction lumen 52, as well as cavity 24 and vacuum ports 46.

When vacuum pressure is applied to cavity 24 via vacuum ports 46, the cavity captures urethral and prostate tissue. Ablation probe 48 is then inserted into the captured tissue. For example, a surgeon may actuate slider bar 34 in manipulator 12 (FIG. 1) to drive ablation probe 48 into the captured tissue. Ablation probe 48 pierces the urethral wall and extends into the target prostate tissue with an orientation substantially parallel to the urethral wall, rater than perpendicular to the urethral wall.

In the example of FIG. 2, ablation probe 48 is an electrically conductive needle that applies electrical current to the captured tissue. In particular, electrical current flows between ablation probe 48 and a reference electrode coupled to current generator 18 and placed on or within the patient Alternatively, ablation probe 48 may be configured as a bipolar instrument tat carries two or more electrodes for localized current flow. Ablation probe 48 may be a solid or hollow needle. If the needle is hollow, ablation probe 48 also may be used as a suction cannula to remove ablated tissue from cavity 24. As an alternative, ablation probe 48 may be withdrawn from lumen 52 and replaced with a suction cannula.

Figure 4:
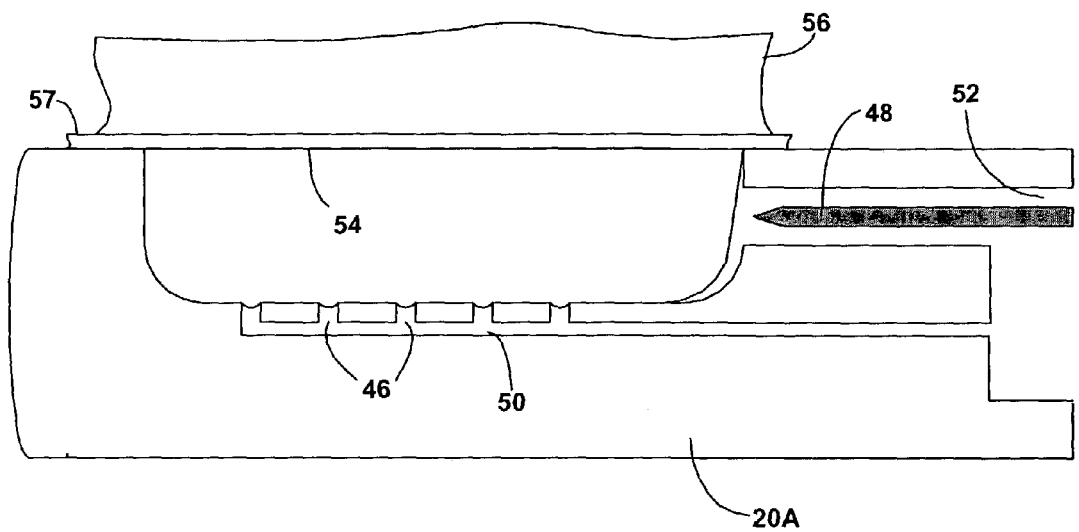
FIG. 4 is an enlarged side view of the distal end of the device of FIG. 1 illustrating engagement of urethral and prostatic tissue.
Figure 5:
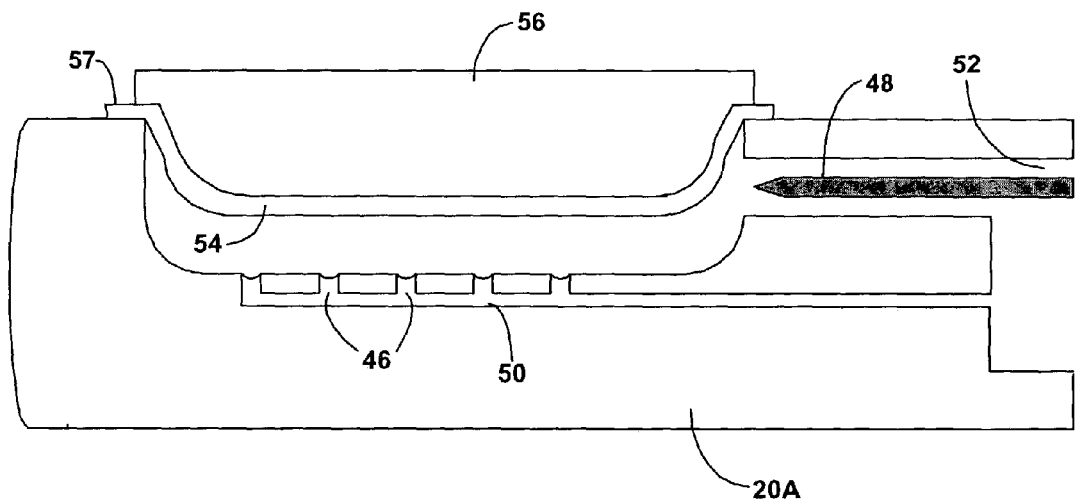
FIG. 5 is an enlarged side view of the distal end of the device of FIG. 1 further illustrating engagement of urethral and prostatic tissue.
Figure 6:
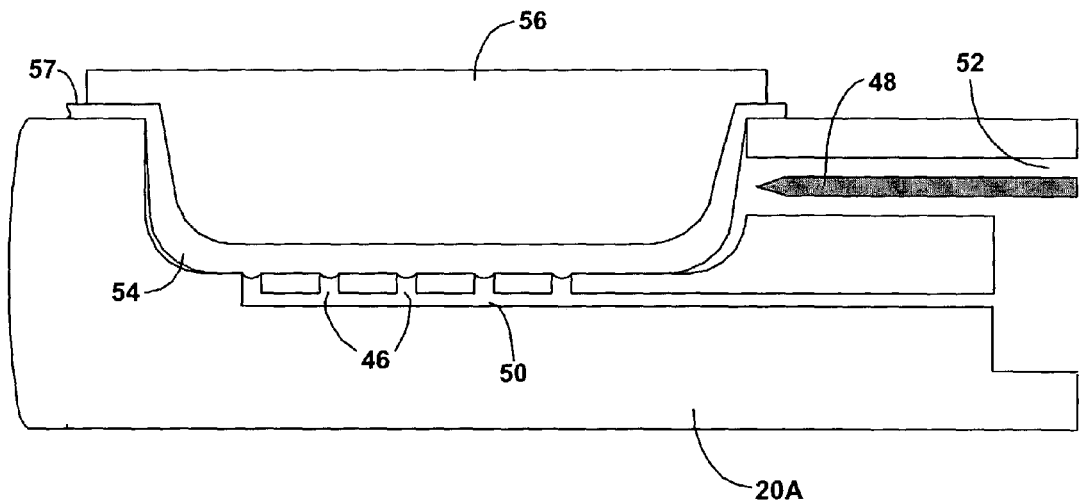
FIG. 6 is an enlarged side view of the distal end of the device of FIG. 1 illustrating capture of urethral and prostatic tissue.

FIGS. 4–6 are enlarged side views of distal end 22 of catheter 20A, illustrating engagement and capture of urethral tissue 54 and prostatic tissue 56 in progressive stages. As shown in FIG. 4, the surgeon initially translates catheter 20A along the length of the urethra to a suitable depth at which cavity 24 comes into substantially longitudinal alignment with a target tissue site. In addition, the surgeon may rotate catheter 20A so that cavity 24 comes into substantial radial alignment with the target tissue site.

The surgeon may initially translate and rotate catheter 20A, for example, to bring cavity 24 into alignment with one of the lateral prostate lobes. As will be described, following ablation of tissue within the desired lobe, the surgeon may rotate catheter 20A to access the other lateral lobe and the medial lobe, if desired. Longitudinal and radial positioning of catheter 20A and cavity 24 may be aided by imaging techniques such as ultrasound, MRI or the like. In addition, in some embodiments, catheter 20A may incorporate an endoscopic imaging device to permit direct acquisition of images from within the urethra.

Once distal end 22 of catheter 20A reaches a desired position, the surgeon activates vacuum source 19 to apply vacuum pressure to vacuum ports 46 via vacuum line 50. As shown in FIG. 5, the vacuum pressure serves to draw urethral wall 54 and prostate tissue 56 into cavity 24. When cavity 24 captures a substantial portion of urethral wall 54 and prostate tissue 56, the vacuum pressure is maintained to hold the captured tissue in place, i.e., to fixate the tissue for the ablation procedure.

Figure 7:
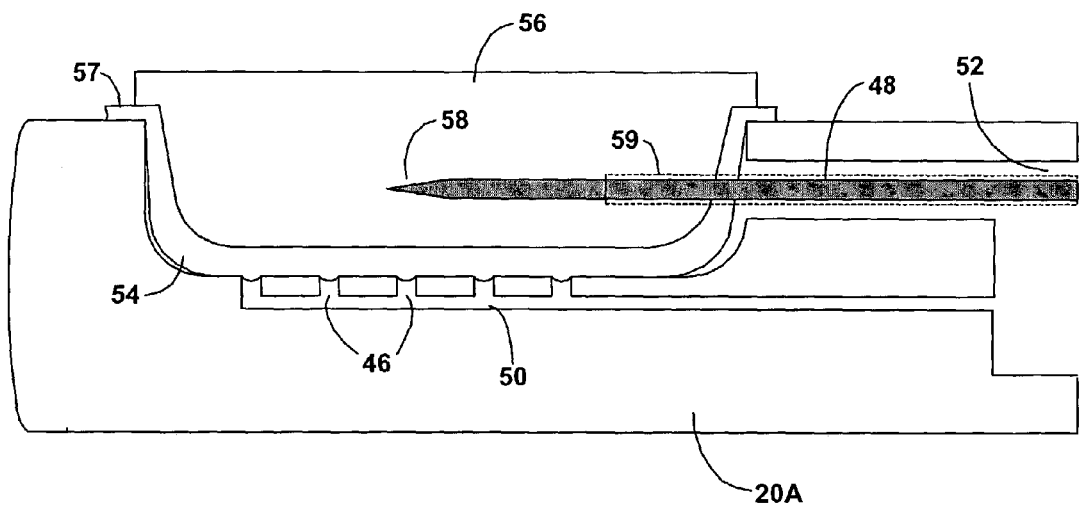
FIG. 7 is an enlarged side view of the distal end of the device of FIG. 1 illustrating introduction of an ablation needle into urethral and prostatic tissue.

FIG. 7 is an enlarged side view of distal end 22 of catheter 20A, illustrating introduction of ablation probe 48 into prostatic tissue 56. The surgeon then actuates slider bar 34 (FIG. 1) or some other actuation device in manipulator 12 to move ablation probe 48 forward and into prostate tissue 56. Once a desired insertion depth is obtained, a distal tip 58 of ablation probe 48 resides at a substantially central position within prostate tissue 56. In particular, distal tip 58 may be positioned at both a central longitudinal position, as well as a central radial position within prostate tissue 56, e.g., with a lateral or medial prostate lobe.

In some embodiments, a portion of ablation probe 48 is insulated, as indicated in FIG. 7 by insulative layer 59, to limit conduction of electrical current to a region more proximal distal tip 58. In particular, insulative layer 59 may prevent substantial conduction of electrical current to urethral tissue 54, avoiding undesirable ablation of the urethral tissue. Distal tip 58 of ablation probe 48 punctures insulative layer 59 upon forward extension of the ablation probe into prostate tissue 56. In this case, ablation probe 48 slides within insulative layer 59. In other embodiments, insulative layer 59 may be coated onto ablation probe 59. Ablation probe 48 also may be coated on the urethral side, along the probe length, to prevent radiation and heating towards the urethral area.

Figure 8:
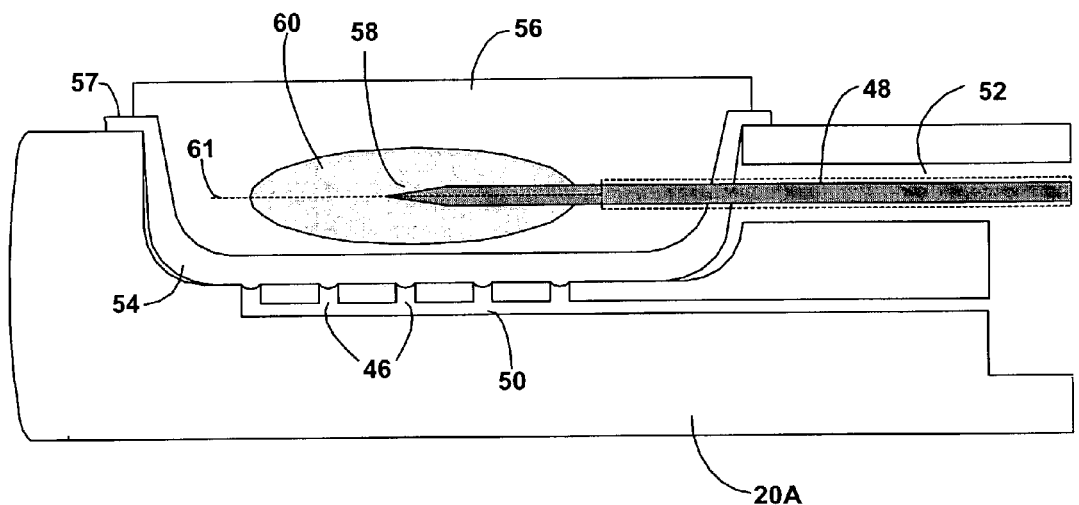
FIG. 8 is an enlarged side view of the distal end of the device of FIG. 1 illustrating ablation of prostatic tissue.

FIG. 8 is an enlarged side view of distal end 22 of catheter 20A, illustrating ablation of a portion of prostatic tissue 56. Upon application of electrical current, ablation probe 48 delivers ablation energy to prostate tissue 56, creating a lesion 60. A major axis 61 of lesion 60 extends substantially parallel to urethral wall 57. As is apparent from FIG. 8, the parallel orientation of ablation probe 48 serves to create a lesion that covers a greater longitudinal extend of prostate tissue 56.

Consequently, catheter 20A ablates a greater extent of prostate tissue 56 in a single step, reducing the time and complexity of the transurethral ablation procedure. In addition, catheter 20A promotes greater precision in the formation of lesion 60 relative to urethral tissue 54 and urethral wall 57. In particular, ablation probe 48 preferably avoids undesirable ablation of urethral tissue 54.

Figure 9:
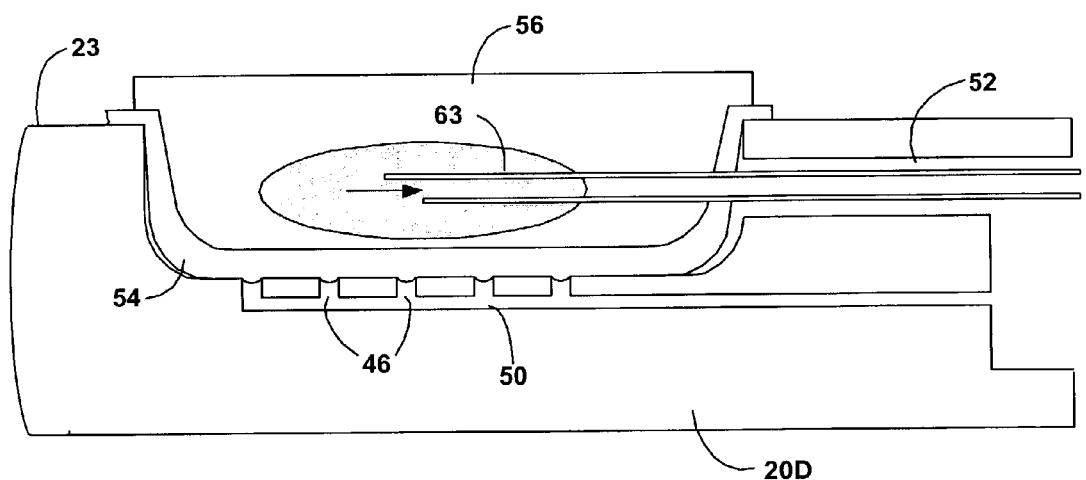
FIG. 9 is an enlarged side view of the distal end of the device of FIG. 1 illustrating the insertion of a suction cannula to remove ablated tissue.

FIG. 9 is an enlarged side view of the distal end of catheter 20A illustrating the insertion of a suction cannula 63 to remove ablated tissue. In particular, following ablation of a portion of prostate tissue 56 by ablation probe 48, the surgeon may withdraw the ablation probe from catheter 20A, and replace it with suction cannula 63. Suction cannula 63 is coupled to a vacuum source and suctions out ablated tissue to reduce the mass and volume of prostate tissue 56, and thereby relieve urethral constriction in the area proximate the prostate tissue.

As an alternative to suction, an auger-like mechanical device could be used to remove ablated prostate tissue. In either case, removal of the ablated tissue can accelerate the therapeutic effects of the procedure. For example, there is less ablated tissue for the body to absorb. Rather, a substantial portion of the ablation tissue can be removed immediately.

Figure 10:
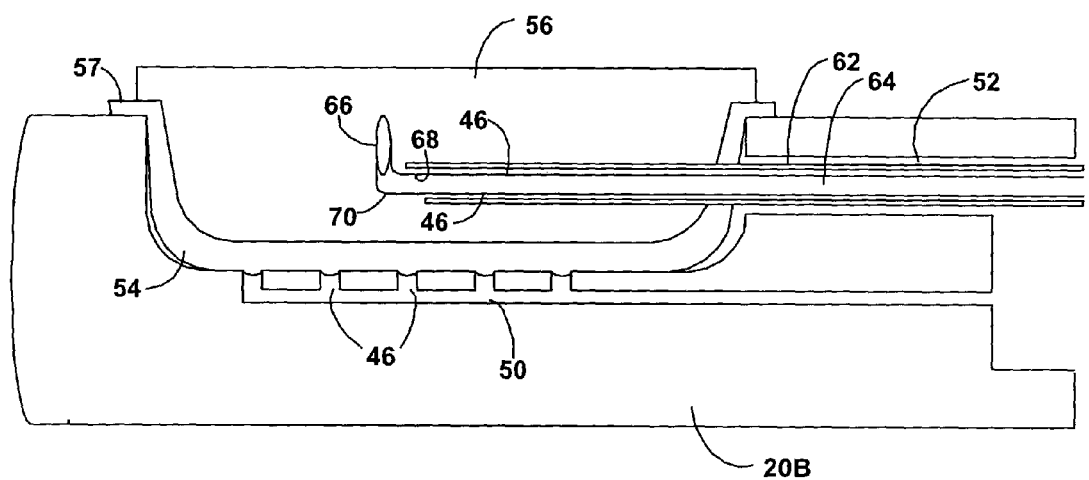
FIG. 10 is an enlarged side view of the distal end of the device of FIG. 1 according to an alternative embodiment of the invention employing an electrosurgery cutting tool.

FIG. 10 is an enlarged side view of the distal end 22 of a catheter 20B according to an alternative embodiment of the invention. In the example of FIG. 10, the ablation probe comprises a stylet 62 defining an inner lumen 64 that houses an electrosurgery cutting tool in the form of electrocautery loop 66. Loop 66 may be used to ablate and resect prostate tissue, e.g., before tissue necrosis if the intention is to use an electrocautery device instead of an ablation device to affect tissue. Alternatively, loop 66 may be used following application of ablation energy by another ablation probe. In particular, once the tissue has been ablated and tissue necrosis has occurred, the tissue can be cut or destructured via cautery loop 66. Sub-mucosa tissue can then be removed by a suction cannula or auger-like device without causing harm to the mucosa layer of the urothelium.

When cavity 24 captures urethral tissue 54 and prostate tissue 56, the surgeon extends stylet 62 into the prostate tissue. Accordingly, a distal end of stylet 62 maybe sufficiently sharp to pierce urethral wall 57 and prostate tissue 56. When the distal stylet 62 reaches the desired position within prostate tissue 56, the surgeon extends electrocautery loop 66 from stylet 62. In the example of FIG. 10, electrical conductors 68, 70 coupled electrocautery loop 66 to current generator 18.

Electrocautery loop 66 and conductors 68, 70 may be formed from a shape memory alloy such as Nitinol. The use of shape memory alloy permits the electrocautery loop to assume a desired shape upon extension from stylet 62, or upon application of a sufficient amount of electrical current by conductors 68, 70. The surgeon rotates or otherwise moves electrocautery loop 66, during application of electrical current, to cut a swath within prostate tissue 56. In some embodiments, the surgeon translates stylet along the length of prostate tissue 56 to cause necrosis of tissue within an elongated zone.

Figure 11:
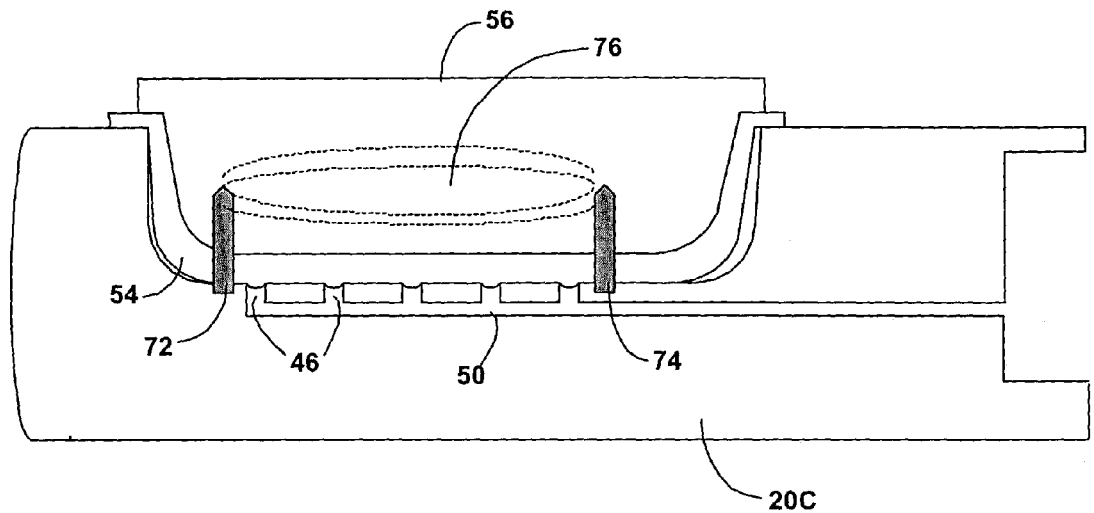
FIG. 11 is an enlarged side view of the distal end of the device of FIG. 1 according to an alternative embodiment of the invention employing multiple needle electrodes.

FIG. 11 is an enlarged side view of distal end 22 of a catheter 20C according to an alternative embodiment of the invention employing multiple needle electrodes oriented perpendicular to urethral wall 57. In the example of FIG. 11, a first needle electrode 72 is mounted adjacent a distal end of cavity 24, and second needle electrode 74 is mounted adjacent a proximal end of cavity 24. Each needle electrode 72, 74 is coupled to current source 18 via electrical conductors (not shown) that extend along the length of catheter 20C.

In operation, needle electrodes 72, 74 pierce urethral tissue 54 and prostate tissue 56 as the tissue is drawn into cavity 24. Alternatively, needle electrodes 72, 74 may be extended from the bottom of cavity 24 upward into urethral tissue 54 and prostate tissue 56 following capture of the tissue by the cavity. In either case, current generator 18 applies electrical current that travels between needle electrodes, as indicated by propagation pattern 76, to ablate a region of prostate tissue 56. Although catheter 20C of FIG. 11 does not make use of a parallel needle orientation, as shown in FIGS. 2–10, needle electrodes 72, 74 still are effective in creating a longitudinally oriented lesion within prostate 56, enhancing precision and reducing the need for a large number of ablation steps.

As an advantage, the incorporation of multiple needle electrodes 72, 74 eliminates the need for a return electrode. Accordingly, the patient does not need to wear an uncomfortable return ground pad, there is no additional preparation in placing the ground pad, and there is no need to monitor the ground pad for proper electrical contact during the course of the procedure.

Figure 12:
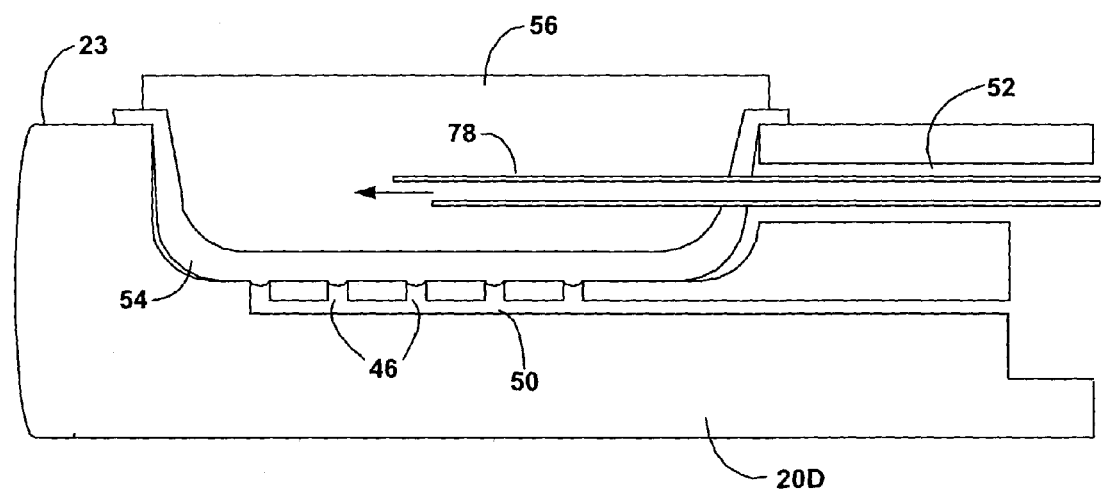
FIG. 12 is an enlarged side view of the distal end of the device of FIG. 1 according to an alternative embodiment of the invention employing a fluid introduction needle.

FIG. 12 is an enlarged side view of distal end 22 of a catheter 20D employing a fluid introduction needle 78. Fluid introduction needle 78 pierces prostate tissue 56 upon capture of the prostate tissue within cavity 24, and facilitates introduction of any of a variety of fluid substances capable of producing necrosis or other therapeutic effects within the prostate tissue. Examples of substances that may be delivered via fluid introduction needle 78 include chemotherapeutic agents, radioactive agents, tissue dissolving agents, and the like. In effect, fluid introduction needle 78 provides an ablation probe, but employs different chemical or biological substances as the ablation agent.

As an example, fluid introduction needle 78 may deliver alcohol or tissue dissolving agents to kill prostate tissue cells for BPH therapy. In each case, the parallel orientation of fluid introduction needle 78 permits a longitudinal zone of tissue to be ablated within prostate tissue 56, and can avoid extensive contact of the fluid with urethral wall 57. In this manner, catheter 20D provides enhanced precision and may reduce the time and number of steps required to achieve a desired degree of ablation. As a further alternative, fluid introduction needle 78 may be used to deliver genes, proteins, and other biological materials, as well as radiation-selective substances, radioactive seeds and the like.

Figure 13:
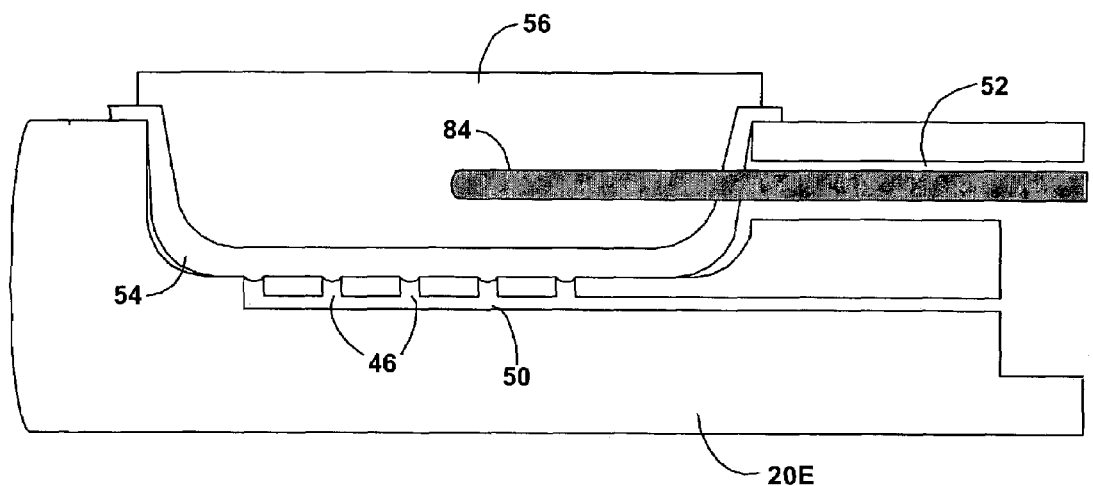
FIG. 13 is an enlarged side view of the distal end of the device of FIG. 1 according to an alternative embodiment of the invention employing an optical waveguide.

FIG. 13 is an enlarged side view of distal end 22 of a catheter 20E of FIG. 1 according to an alternative embodiment of the invention employing an optical waveguide 84 as an ablation probe. In the example of FIG. 13, the surgeon advances optical waveguide 84 into the captured prostate tissue 56, and delivers laser energy via the waveguide to ablate prostate tissue. Optical waveguide 84 may emit the laser energy with a wavelength and amplitude suitable for ablation via a distal tip of the waveguide. For example, the laser energy may have a wavelength in the range of approximately 800 to 850 nanometers. In addition, optical waveguide 84 may have cladding removed in a selected region to enable lateral emission, i.e., side-firing laser emission. In either case, optical waveguide 84 is oriented substantially parallel to urethral wall 57, enabling formation of an elongated lesion with significant precision.

Figure 14:
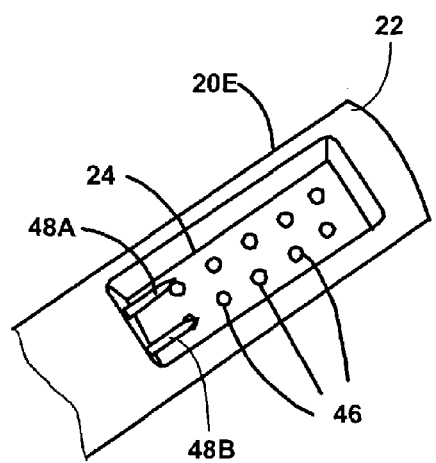
FIG. 14 is an enlarged perspective view of the distal end of the device of FIG. 1 according to an alternative embodiment employing multiple ablation probes.

FIG. 14 is an enlarged perspective view of distal end 22 of a catheter 20E having multiple ablation probes 48A, 48B. Ablation probes 48A, 48B are disposed side-by-side and may take the form of any of the various ablation probes depicted in FIGS. 2–13. In an alternative embodiment, ablation probes 48A, 48B may form a bipolar electrode needle arrangement. Alternatively, ablation probes 48A, 48B may emit electrical current at the same polarity for transmission to a reference electrode placed on or within the patient. Each ablation probe 48A, 48B may be extended into prostate tissue within cavity 24. In addition to the ability to form a longitudinal lesion with the prostate tissue, ablation probes 48A, 48B form lesions at different radial positions with the prostate tissue. In this manner, catheter 20E of FIG. 14 provides a larger volume of ablated tissue in a single step, and still affords the advantages of precision, which can prevent significant ablation of the urethral wall.

Figure 15:
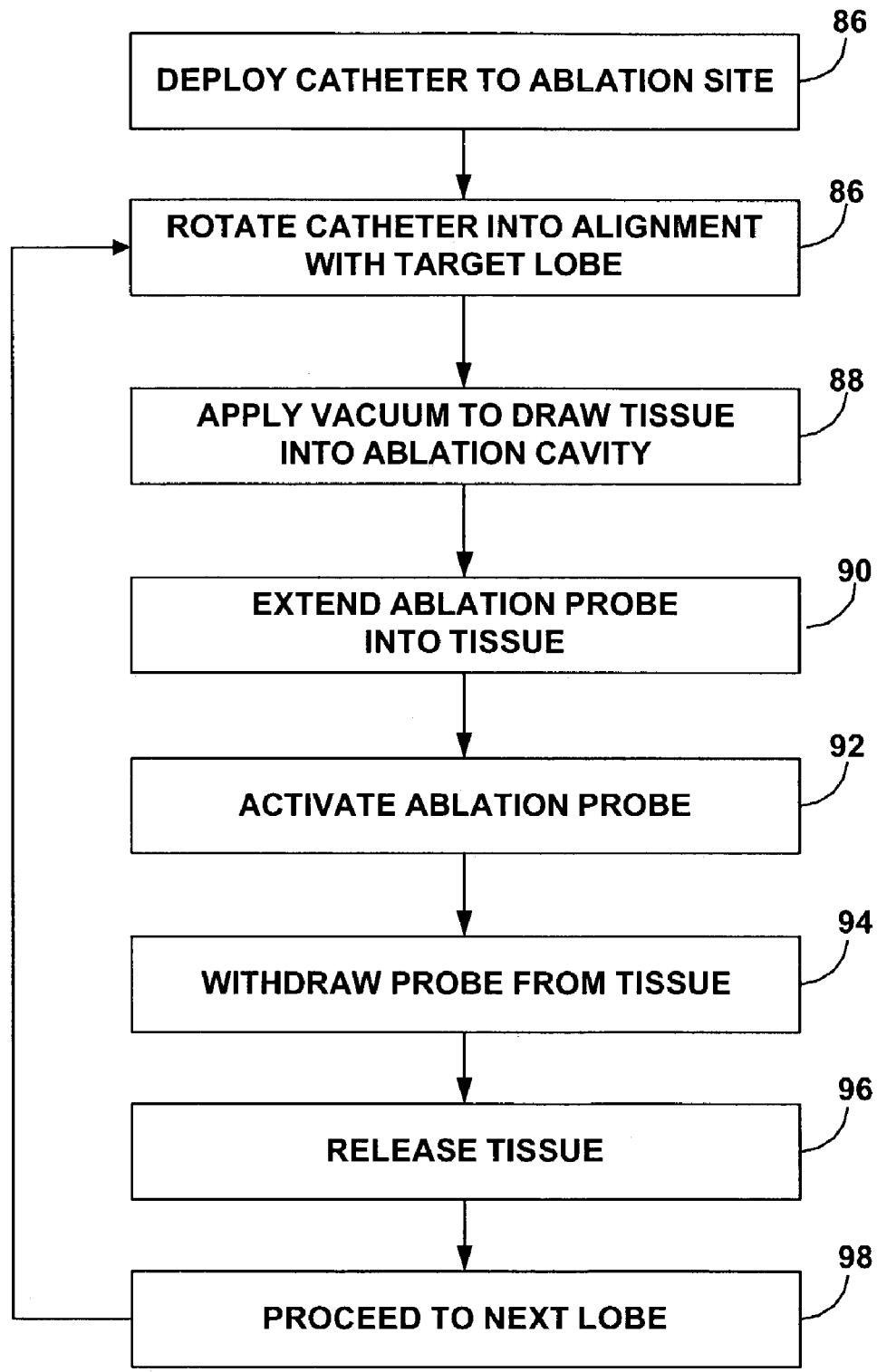
FIG. 15 is a flow diagram illustrating a transurethral ablation procedure.

FIG. 15 is a flow diagram illustrating a transurethral ablation procedure. As shown in FIG. 15, the transurethral ablation procedure involves deploying a catheter to an ablation site (85), i.e., providing longitudinal alignment of cavity 24 with a site within the urethra adjacent the prostate. Upon rotating the catheter into radial alignment with a desired prostate lobe (86), the procedure further involves application of vacuum pressure to draw the tissue into an ablation cavity formed in the catheter (88). Once the tissue has been capture, the procedure involves extending an ablation tissue into the captured tissue (90), and activating the ablation probe (92), e.g., by delivery of electrical current, laser energy, fluid agents, or the like. Following delivery of a suitable amount of ablation energy, or fluid in some embodiments, the ablation probe is withdrawn from the tissue (94), and the tissue is released from the cavity (96). At this point, the surgeon can choose to proceed to ablation of another prostate lobe (98), e.g., by rotating the catheter to bring the cavity into alignment with the desired lobe (86) and repeating the ablation process.

Figure 16:
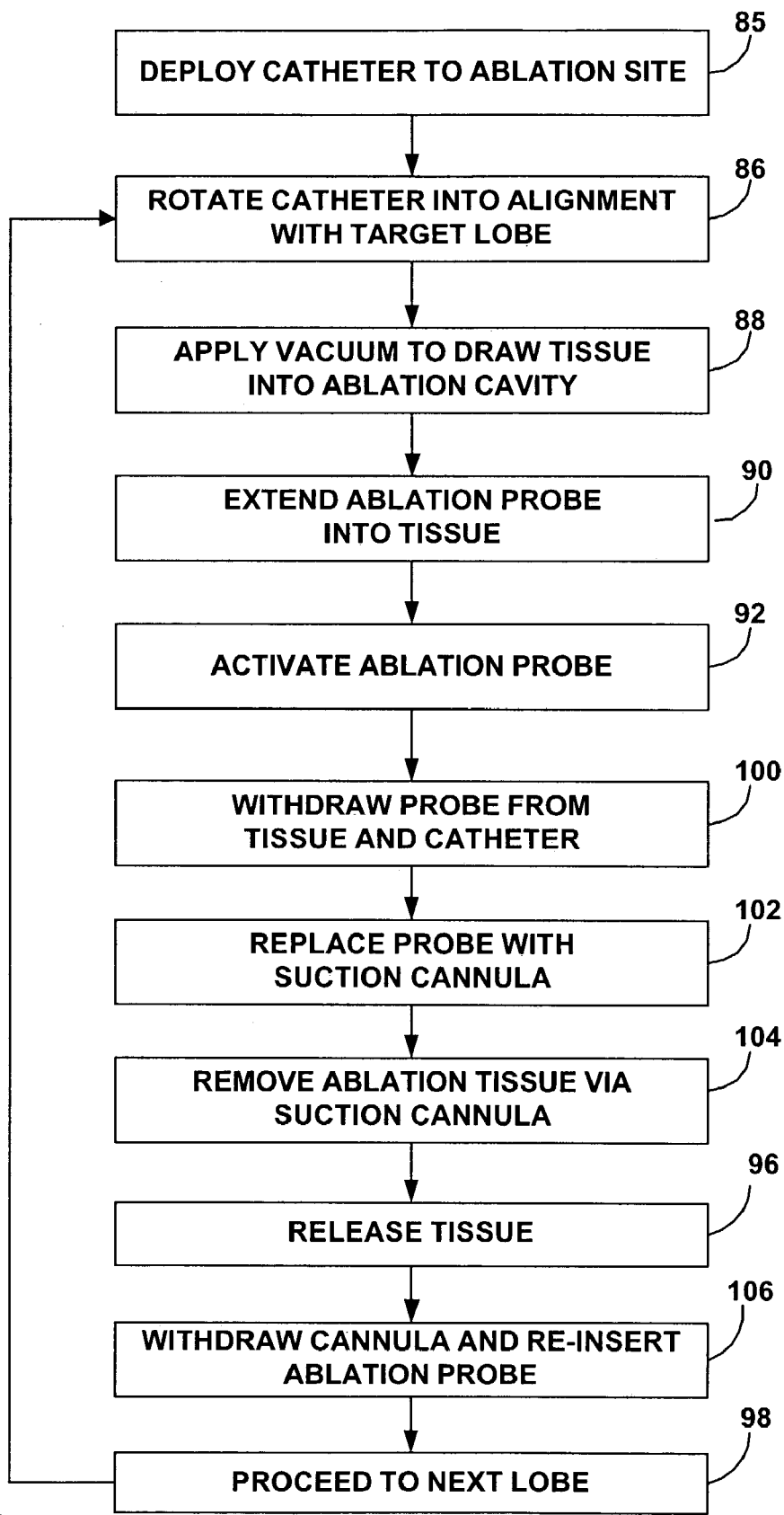
FIG. 16 is a flow diagram illustrating another transurethral ablation procedure.

FIG. 16 is a flow diagram illustrating another transurethral ablation procedure. The procedure of FIG. 16 conforms substantially to the procedure of FIG. 15. The procedure of FIG. 16 further includes, however, the step of withdrawing the ablation probe from the catheter (100), replacing it with a suction cannula (102) and removing ablated tissue from the tissue site via the suction cannula (104). Then, the suction cannula can be withdrawn and the ablation probe can be re-inserted into the catheter for ablation of another tissue site (106) following release of the tissue from the cavity in the catheter (96).

Removal of ablated tissue using a suction cannula can accelerate the therapeutic effects of the transurethral ablation procedure by reducing the mass, and possibly the volume, in the area of the lesion created by the ablation probe. In some embodiments, an auger-like mechanical device may be used, instead of a suction cannula, to remove ablated tissue from the tissue site. In either case, with immediate reduction of mass and volume, the transurethral ablation procedure may offer early relief of the urethral constriction created by the prostate tissue. As an alternative, the ablation probe may take the form of a hollow needle or stylet that defines an inner lumen for removal of ablated tissue with withdrawing the ablation probe from the catheter. In other words, the ablation probe may be integrally formed with a suction cannula. As another alternative, the ablation probe and suction cannula may occupy separate channels within the catheter, avoiding the need to remove one for use of the other.

Additional features may include one or more internal lumens within the catheter for delivery of cooling agents to the area proximate the urethra to protect the urethra from tissue necrosis during ablation of prostatic tissue. Selective cooling of the urethral tissue may serve to help control the size of the lesion formed by the ablation probe within the prostate tissue. Also, if a suction cannula is provided, the cannula may be used both for removal of ablated tissue and irrigation of the ablation site before or after removal of the ablated tissue.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems for transurethral ablation, as described herein.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A method comprising:
   inserting a distal end of a catheter into a urethra of a male patient, wherein the distal end of the catheter defines a lateral cavity;
   moving the distal end of the catheter to a position within the urethra proximate to the prostate;
   applying vacuum pressure to the cavity to capture a portion of the urethra and a portion of the prostate into the cavity;
   inserting an ablation probe into the captured portion of the prostate via the catheter; and
   ablating tissue within the prostate beneath the prostatic urethra via the ablation probe.

2. The method of claim 1, further comprising inserting the ablation probe into the captured portion of the prostate with an orientation substantially parallel to a wall of the urethra proximate the prostate.

3. The method of claim 1, wherein inserting an ablation probe includes inserting two or more ablation probes into the captured portion of the prostate.

4. The method of claim 3, wherein the ablation probes are electrically conductive, and ablating tissue within the prostate includes applying electrical current between the ablation probes.

5. The method of claim 3, further comprising inserting the ablation probes into the captured portion of the prostate with orientations substantially parallel to a wall of the urethra proximate the prostate.

6. The method of claim 3, further comprising inserting the ablation probes into the captured portion of the prostate with orientations substantially perpendicular to a wall of the urethra proximate the prostate.

7. The method of claim 1, wherein ablating tissue within the prostate includes delivering electrical current to the prostate via the ablation probe.

8. The method of claim 1, wherein ablating tissue within the prostate includes delivering microwave energy to the prostate via the ablation probe.

9. The method of claim 1, wherein ablating tissue within the prostate includes delivering laser energy to the prostate via the ablation probe.

10. The method of claim 1, wherein ablating tissue within the prostate includes delivering a chemical ablation agent to the prostate via the ablation probe.

11. The method of claim 1, wherein the ablation probe include an electrosurgery blade, and ablating tissue within the prostate includes delivering current to the prostate via the electrosurgery blade.

12. The method of claim 11, further comprising rotating the electrosurgery blade to cut prostate tissue.

13. The method of claim 1, further comprising rotating the catheter into radial alignment with a target portion of the urethra and a target portion of the prostate before applying the vacuum pressure.

14. The method of claim 1, further comprising:
withdrawing the ablation probe from the captured portion of the prostate;
deactivating the application of vacuum pressure to the cavity;
rotating the catheter into radial alignment with a second portion of the urethra and a second portion of the prostate;
reactivating the application of vacuum pressure to the cavity to capture the second portion of the urethra and the second portion of the prostate into the cavity;
inserting the ablation probe into the captured second portion of the prostate via the catheter; and
ablating tissue within the second portion of the prostate beneath the prostatic urethra via the ablation probe.

15. The method of claim 1, further removing a portion of the ablated tissue via a suction cannula within the catheter.

16. The method of claim 1, further comprising:
withdrawing the ablation probe;
inserting a suction cannula into the captured portion of the prostate via the catheter; and
removing a portion of the ablated tissue via the suction cannula.

17. A transurethral ablation device comprising:
a catheter sized for insertion into a urethra of a male patient, wherein a distal end of the catheter defines a lateral cavity;
a vacuum line to apply vacuum pressure to the cavity to capture a portion of the urethra and a portion of the prostate into the cavity; and
an ablation probe having a distal tip mounted within the catheter adjacent the cavity, wherein the ablation probe is movable for insertion into the captured portion of the prostate.

18. The device of claim 17, wherein the ablation probe is oriented for insertion into the captured portion of the prostate in a direction substantially parallel to a wall of the urethra proximate the prostate.

19. The device of claim 17, wherein the ablation probe includes two or more ablation probes.

20. The device of claim 19, wherein the ablation probes are electrically conductive, and electrical current travels between the ablation probes within the captured portion of the prostate upon application of the electrical current to one or both of the ablation probes.

21. The device of claim 19, wherein the ablation probes are oriented for insertion into the captured portion of the prostate in a direction substantially perpendicular to a wall of the urethra proximate the prostate.

22. The device of claim 19, wherein the ablation probe is oriented for insertion into the captured portion of the prostate in a direction substantially parallel to a wall of the urethra proximate the prostate.

23. The device of claim 17, further comprising an electrical conductor to deliver electrical current to the ablation probe for ablation of tissue within the prostate.

24. The device of claim 17, further comprising an electrical conductor to deliver microwave energy to the ablation probe for ablation of tissue within the prostate.

25. The device of claim 17, comprising an optical waveguide to deliver laser energy to the prostate via the ablation probe.

26. The device of claim 17, further comprising a fluid delivery cannula to deliver a chemical ablation agent to the prostate via the ablation probe.

27. The device of claim 17, wherein the ablation probe include an electrosurgery blade, the device further comprising an electrical conductor to deliver electrical current to the prostate via the electrosurgery blade.

28. The device of claim 27, wherein the electrosurgery blade is rotatable to cut prostate tissue.

29. The device of claim 17 wherein the catheter is rotatable to bring the cavity into radial alignment with a target portion of the urethra and a target portion of the prostate before application of the vacuum pressure via the vacuum line.

30. The device of claim 17, further comprising a suction cannula within the catheter for removal of a portion of the ablated tissue.

31. The device of claim 30, wherein the catheter defines a lumen to accommodate the ablation probe and, upon removal of the ablation probe, the suction cannula.

32. The device of claim 30, wherein the ablation probe comprises a hollow needle and the suction cannula is integrated with the needle.

33. The device of claim 32, wherein an interior lumen of the ablation probe defines an interior lumen of the suction cannula.

34. A method comprising:
inserting an ablation probe into a target site within a prostate at an orientation substantially parallel to a portion of the urethral wall adjacent the prostate;
applying ablation energy to the prostate beneath the portion of the urethral wall via the ablation probe to form a lesion having a major axis that extends substantially parallel to the portion of the urethral wall beneath the prostate; and removing ablated tissue from the target site via a suction cannula.

35. The method of claim 34, wherein applying ablation energy includes delivering electrical current to the prostate via the ablation probe.

36. The method of claim 34, wherein applying ablation energy includes delivering microwave energy to the prostate via the ablation probe.

37. The method of claim 34, wherein applying ablation energy includes delivering laser energy to the prostate via the ablation probe.

38. The method of claim 34, further comprising rotating the catheter into radial alignment with a second target site, and applying ablation energy via the ablation probe to form a lesion within the second target site.

39. The method of claim 34, further comprising:
    withdrawing the ablation probe;
    inserting the suction cannula into the target site; and
    removing a portion of the ablated tissue via the suction cannula.

40. A transurethral ablation device comprising:
    a catheter sized for insertion into a urethra of a male patient wherein a distal end of the catheter defines a lateral cavity;
    a vacuum line to apply vacuum pressure to the cavity to capture a portion of the urethra and a portion of the prostate into the cavity; and
    an ablation probe having a distal tip mounted within the catheter adjacent the cavity, wherein the ablation probe is movable for insertion into the captured portion of the prostate
    wherein the lateral cavity and the ablation probe are configured to ablate the pro static tissue beneath the urethra.

* * * * *